(12) United States Patent
Karthikeyan

(10) Patent No.: US 9,558,403 B2
(45) Date of Patent: Jan. 31, 2017

(54) CHEMICAL STRUCTURE RECOGNITION TOOL

(75) Inventor: Muthukumarasamy Karthikeyan, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 162 days.

(21) Appl. No.: 14/241,285

(22) PCT Filed: Aug. 27, 2012

(86) PCT No.: PCT/IN2012/000567
§ 371 (c)(1),
(2), (4) Date: May 20, 2014

(87) PCT Pub. No.: WO2013/030850
PCT Pub. Date: Mar. 7, 2013

(65) Prior Publication Data
US 2014/0301608 A1 Oct. 9, 2014

(30) Foreign Application Priority Data
Aug. 26, 2011 (IN) ............................ 2420/DEL/2011

(51) Int. Cl.
*G06K 9/00* (2006.01)
*G06K 9/36* (2006.01)
(Continued)

(52) U.S. Cl.
CPC ......... *G06K 9/00476* (2013.01); *G06F 19/708* (2013.01); *G06K 9/3216* (2013.01); *G06K 9/72* (2013.01); *G06K 2209/01* (2013.01)

(58) Field of Classification Search
None
See application file for complete search history.

(56) References Cited

U.S. PATENT DOCUMENTS 5,157,736 A * 10/1992 Boyer ................ G06K 9/00476
382/113
5,790,691 A * 8/1998 Narayanswamy . G06K 9/00127
382/133
(Continued)

OTHER PUBLICATIONS

"International Application No. PCT/IN2012/000567, Article 19 Amendment filed Oct. 14, 2013", (Oct. 14, 2013), 5 pgs.
(Continued)

*Primary Examiner* — Matthew Bella
*Assistant Examiner* — Jose M Torres
(74) *Attorney, Agent, or Firm* — Schwegman Lundberg & Woessner, P.A.

(57) ABSTRACT

A method of extracting and then reusing/remodeling chemical data from a hand written or digital input image without manual inputs using Chemical Structure Recognition Tool (CSRT) is disclosed herein. It comprises loading said input image, converting said input image into a grayscale image i.e. stretching of loaded input image, converting said grayscale image into a binary image i.e. binarization, smoothing to reduce noise within said binary image, recognizing circle bond to identify presence of a circle inside a ring, predicting OCR region to find zones containing text, image thinning to identify specific shapes within said binary image, edge detection to detect image contrast, detecting double and triple bond, and obtaining output files.

8 Claims, 12 Drawing Sheets

(51) Int. Cl.
*G06F 19/00* (2011.01)
*G06K 9/32* (2006.01)
*G06K 9/72* (2006.01)

(56) References Cited

U.S. PATENT DOCUMENTS

| | | | | |
|---|---|---|---|---|
| 5,870,495 | A | * | 2/1999 | Mancuso ............ G06K 9/4633 382/199 |
| 2004/0021700 | A1 | * | 2/2004 | Iwema ............... G06K 9/00436 715/863 |
| 2009/0304282 | A1 | * | 12/2009 | Predovic ............ G06K 9/00463 382/187 |
| 2010/0163316 | A1 | | 7/2010 | Chang et al. |
| 2011/0202331 | A1 | | 8/2011 | Lawson et al. |
| 2011/0276589 | A1 | * | 11/2011 | Smith .................. G06F 19/705 707/769 |
| 2012/0141032 | A1 | * | 6/2012 | Ouyang ............ G06K 9/00422 382/187 |

OTHER PUBLICATIONS

"International Application No. PCT/IN2012/000567, International Search Report mailed Aug. 14, 2013", (Aug. 14, 2013), 5 pgs.

Algorri, M. E, et al., "Reconstruction of Chemical Molecules from Images", 29th Annual International Conference of the IEEE Engineering in Medicine and Biology Society, 2007. EMBS 2007., (2007), 4609-4612.

Algorri, Maria-Elena, "Automatic Recognition of Chemical Images", IEEE Computer Society: Eighth Mexican Int'l Conference on Current Trends in Computer Science Proceedings, Morelia, Michoacan, Mexico, (Sep. 2007), 41-46.

Casey, R., et al., "Optical Recognition of Chemical Graphics", Proceedings of the Second International Conference on Document Analysis and Recognition, (Oct. 20, 1993), 627-631.

Filippov, I. V, et al., "Optical Structure Recognition Software to Recover Chemical Information: OSRA, An Open Source Solution", J. Chem. Inf. Model., 49(3), (2009), 740-743.

McDaniel, Joe R, et al., "Automatic interpretation of chemical structure diagrams", Graphics Recognition Methods and Applications, Lecture Notes in Computer Science, vol. 1072, (1996), 148-158.

McDaniel, Joe R., et al., "Kekule: OCR-optical chemical (structure) recognition", J. Chem. Inf. Comput. Sci., 32(4), (1992), 373-378.

Park, J., et al., "Automated extraction of chemical structure information from digital raster images", Chem Cent J., 3, (Feb. 5, 2009), 4.

Valko, A. T, et al., "CLiDE Pro: the latest generation of CLiDE, a tool for optical chemical structure recognition", J Chem Inf Model., 49(4), (Apr. 2009), 780-7.

* cited by examiner

Automatic recognition 3D generation, Name & Property prediction

```
chemrobot@NCL-Pune-India    290711121820
16 18  0  0  0  0               999 V2000
   -2.9300   -3.3900    0.0000 C   0  0  0  0  0  0  0  0  0  0  0  0
   -2.4300   -3.3900    0.0000 O   0  0  0  0  0  0  0  0  0  0  0  0
   -4.1200   -2.2400    0.0000 N   0  0  0  0  0  0  0  0  0  0  0  0
   -3.6300   -2.2400    0.0000 N   0  0  0  0  0  0  0  0  0  0  0  0
   -2.6800   -2.4800    0.0000 C   0  0  0  0  0  0  0  0  0  0  0  0
   -2.6800   -1.7700    0.0000 C   0  0  0  0  0  0  0  0  0  0  0  0
   -3.2900   -1.4100    0.0000 C   0  0  0  0  0  0  0  0  0  0  0  0
   -3.2900   -0.7200    0.0000 C   0  0  0  0  0  0  0  0  0  0  0  0
   -2.0700   -1.4200    0.0000 C   0  0  0  0  0  0  0  0  0  0  0  0
   -2.0700   -0.7200    0.0000 C   0  0  0  0  0  0  0  0  0  0  0  0
   -2.6800   -0.3500    0.0000 C   0  0  0  0  0  0  0  0  0  0  0  0
   -2.6800    0.1100    0.0000 O   0  0  0  0  0  0  0  0  0  0  0  0
   -3.2100   -3.9000    0.0000 O   0  0  0  0  0  0  0  0  0  0  0  0
   -3.7000   -3.0800    0.0000 C   0  0  0  0  0  0  0  0  0  0  0  0
   -3.2700   -2.8200    0.0000 C   0  0  0  0  0  0  0  0  0  0  0  0
   -3.6900   -0.4700    0.0000 O   0  0  0  0  0  0  0  0  0  0  0  0
  1  2  2  0  0  0
  3  4  1  0  0  0
  5  6  1  0  0  0
  7  8  4  0  0  0
  9 10  4  0  0  0
 11 12  1  0  0  0
 13  1  1  0  0  0
 14 15  1  0  0  0
 15  5  1  0  0  0
  6  9  4  0  0  0
  8 11  4  0  0  0
 15  1  1  0  0  0
  4 15  1  0  0  0
  7  6  4  0  0  0
 16  8  1  0  0  0
 11 10  4  0  0  0
M  END0>  <image_file_name>8903.jpg0>  <SOURCE>8http://moltable.ncl.res.in8$$$$8
```

Figure 7

```
6',7'-dimethoxy-3',4'-dihydro-2'H-spiro[cyclohexane-1,1'-naphthalene]-2,6-dione
  chemrobot@BCL-Pune-India   082411124926

21 23  0  0  0  0              999 V2000
     6.5089   -0.4135    0.0000 C   0  0  0  0  0  0  0  0  0  0  0  0
     5.8853    0.1276    0.0000 O   0  0  0  0  0  0  0  0  0  0  0  0
     5.1057   -0.1425    0.0000 C   0  0  0  0  0  0  0  0  0  0  0  0
     4.4821    0.3976    0.0000 C   0  0  0  0  0  0  0  0  0  0  0  0
     4.6380    1.2078    0.0000 C   0  0  0  0  0  0  0  0  0  0  0  0
     5.4173    1.4778    0.0000 C   0  0  0  0  0  0  0  0  0  0  0  0
     3.7025    0.1276    0.0000 C   0  0  0  0  0  0  0  0  0  0  0  0
     3.5466   -0.6825    0.0000 C   0  0  0  0  0  0  0  0  0  0  0  0
     4.1702   -1.2226    0.0000 C   0  0  0  0  0  0  0  0  0  0  0  0
     4.0143   -2.0328    0.0000 C   0  0  0  0  0  0  0  0  0  0  0  0
     3.2348   -2.3028    0.0000 C   0  0  0  0  0  0  0  0  0  0  0  0
     2.6111   -1.7627    0.0000 C   0  0  0  0  0  0  0  0  0  0  0  0
     2.7671   -0.9526    0.0000 C   0  0  0  0  0  0  0  0  0  0  0  0
     1.9875   -1.2226    0.0000 C   0  0  0  0  0  0  0  0  0  0  0  0
     1.8316   -2.0328    0.0000 O   0  0  0  0  0  0  0  0  0  0  0  0
     1.3639   -0.6825    0.0000 C   0  0  0  0  0  0  0  0  0  0  0  0
     1.5198    0.1276    0.0000 C   0  0  0  0  0  0  0  0  0  0  0  0
     2.2993    0.3976    0.0000 C   0  0  0  0  0  0  0  0  0  0  0  0
     2.9230   -0.1425    0.0000 C   0  0  0  0  0  0  0  0  0  0  0  0
     3.3949    0.5343    0.0000 O   0  0  0  0  0  0  0  0  0  0  0  0
     4.9498   -0.9526    0.0000 C   0  0  0  0  0  0  0  0  0  0  0  0
  1  2  1  0  0  0
  2  3  1  0  0  0
  3  4  2  0  0  0
  4  5  1  0  0  0
  5  6  1  0  0  0
  4  7  1  0  0  0
  7  8  2  0  0  0
  8  9  1  0  0  0
  9 10  1  0  0  0
 10 11  1  0  0  0
 11 12  1  0  0  0
 12 13  1  0  0  0
  8 13  1  0  0  0
 13 14  1  0  0  0
 14 15  2  0  0  0
 14 16  1  0  0  0
 16 17  1  0  0  0
 17 18  1  0  0  0
 18 19  1  0  0  0
 13 19  1  0  0  0
 19 20  2  0  0  0
  9 21  2  0  0  0
  3 21  1  0  0  0
> <NAME>
6',7'-dimethoxy-3',4'-dihydro-2'H-spiro[cyclohexane-1,1'-naphthalene]-2,6-dione
> <SMILES>
COC1=C(OC)C=C2C(CCCC22C(=O)CCCC2=O)=C1

M  END
```

Figure 18

CHEMICAL STRUCTURE RECOGNITION TOOL

PRIORITY CLAIM TO RELATED APPLICATIONS

This application is a national stage application under 35 U.S.C. §371 of PCT/IN2012/000567, filed Aug. 27, 2012, and published as WO 2013/030850 on Mar. 7, 2013, which claims priority to India Application No. 2420/DEL/2011, filed Aug. 26, 2011, which applications and publication are incorporated by reference as if reproduced herein and made a part hereof in their entirety, and the benefit of priority of each of which is claimed herein.

FIELD OF THE INVENTION

The present invention relates to chemical structure recognition tool (CSRT) to recognize molecular structures from files and images. More specifically, the present invention relates to process for harvesting chemical data from hand drawn or digital images and rendering them into suitable forms to reuse said harvested information for simulation and model/remodeling of structure in the field of chemoinformatics.

BACKGROUND OF THE INVENTION

Chemoinformatics plays an important role in areas that rely on topology and information of the chemical space. Many areas concerning discovery and formulation of new materials of drug involve an immense amount of study, modeling and simulation of various chemical structures, formulae, properties and similar aspects for achieving the end result.

Chemoinformatics are often used in pharmaceutical companies in the process of drug discovery or formation. These methods can also be used in chemical and other allied industries for various uses. Interpretation of chemical structures and formulae into computable structures is cumbersome and time consuming and often requires manual intervention. Enormous effort is poured into drafting images in intellectual papers and articles and such images that cannot be further reproduced for computational purposes.

There are some documents which teach to extract data relating to chemical structures. References may be made to Patent Application US2011202331 discloses an invention comprising methods and software for processing text documents and extracting chemical data therein. Preferred method embodiments of said invention comprise: (a) identifying and tagging one or more chemical compounds within a text document; (b) identifying and tagging physical properties related to one or more of those compounds; (c) translating one or more of those compounds into a chemical structure; (d) identifying and tagging one or more chemical reaction descriptions within the text document; and (e) extracting at least some of the tagged information and storing it in a database.

References may be made to an article titled "CLiDE Pro: The Latest Generation of CLiDE, a Tool for Optical Chemical Structure Recognition" by Aniko T. Valko et. al. in J. Chem. Inf. Mod., 2009, 49(4), pp 780-787, discloses an advance version of CLiDE software, CLiDE Pro for extraction of chemical structure and generic structure information from electronic images of chemical molecules available online and pages of scanned documents. The process of extraction has three steps: segmentation of image into text and graphical regions, analysis of graphical region and reconstruction of connection table, and interpretation of generic structures by matching R-groups found in structure diagrams with the ones located in the text.

References may be made to U.S. Pat. No. 5,157,736 discloses an apparatus and methods for optical recognition of chemical graphics which allows documents containing chemical structures to be optically scanned so that both the text and the chemical structures are recognized. In the said invention, the structures are directly converted into molecular structure files suitable for direct input into chemical databases, molecular modeling programs, image rendering programs, and programs that perform real time manipulation of structures. References may be made to a paper titled "Optical recognition of chemical graphics" by Casey R. et. al. appeared in Document Analysis and Recognition, 1993, proceedings of the Second International Conference, discloses a prototype system for encoding chemical structure diagrams from scanned printed documents.

References may be made to a paper titled "Optical recognition of chemical graphics" by Casey R. et. al. appeared in Document Analysis and Recognition, 1993, proceedings of the Second International Conference, discloses a prototype system for encoding chemical structure diagrams from scanned printed documents.

References may be made to an article titled "Automatic Recognition of Chemical Images" by Maria-Elena Algorri, discloses a system that can automatically reconstruct the chemical information associated to the images of chemical molecules thus rendering them computer readable. The system consists of 5 modules: 1) Pre-processing module which binarizes the input image and labels it into its constituent connected components. 2) OCR module which examines the connected components and recognizes those that represent letters, numbers or special symbols. 3) Vectorizer module which converts the connected components not labeled by the OCR into graphs of vectors, 4) Reconstruction module which analyzes the graphs of vectors produced by the vectorizer and annotates the vectors with their chemical significance using a library of chemical graph-based rules. It also analyzes the results of the OCR and groups the letters, numbers and symbols into names of atoms and superatoms and then it associates the chemically annotated vector graphs with the results of the OCR. 5) Chemical Knowledge module which turns the chemically annotated vector graphs into chemical molecules under knowledge-based chemical rules, verifies the chemical validity of the molecules and produces the final chemical files.

References may be made to an Journal "J. Chem. Inf. Model 2009, 49, 740-743", wherein inventor built an optical structure recognition application based on modern advances in image processing implemented in open source tools—OSRA. OSRA can read documents in over 90 graphical formats including GIF, JPEG, PNG, TIFF, PDF, and PS, automatically recognizes and extracts the graphical information representing chemical structures in such documents, and generates the SMILES or SD representation of the encountered molecular structure images.

However, processing of live images using webcams to harvest chemical data from hand drawn images is found to be difficult. There exists a need for a tool to acquire data from digital imaging apparatus and convert them into file formats suitable for reusability in simulation and modeling efficiently.

However, processing of live images using webcams to harvest chemical data from hand drawn images is found to be difficult. There exists a need for a tool to acquire data from digital imaging apparatus and convert them into file formats suitable for reusability in simulation and modeling efficiently.

OBJECTIVES OF THE INVENTION

Main objective of the present invention is to provide chemical structure recognition tool (CSIT) to recognize molecular structures from files and images.

Another objective of the present invention is to provide harvesting of chemical data from hand drawn or digital images and rendering them into suitable forms to reuse said harvested information for simulation and model/remodeling of structure in the field of chemo informatics.

SUMMARY OF THE INVENTION

Accordingly, Present invention provides a Chemical Structure Recognition Tool (CSRT) to extract and reuse/remodel chemical data from a hand written or digital input image without manual inputs, comprising an image scanner, an image manipulator and analyzer.

In an embodiment of the present invention, image scanner is an image acquisition tool, independent or integrated to any devices selected from digital camera, mobile phone, phone camera, computer, scanner and the analyzer and manipulator are the software, independent of the type of image scanner.

In yet another embodiment of the present invention, said input image is accepted and output as a digital image or characteristics associated with such an image by said image scanner.

In yet another embodiment, present invention provides a method of extracting and then reusing/remodeling chemical data from a hand written or digital input image without manual inputs using Chemical Structure Recognition Tool (CSRT) and the said method comprising the steps of:
  a. loading hand written or digital input image by input device;
  b. stretching said input image as loaded in step (a) to obtain grayscale image;
  c. binarizing said grayscale image as obtained in step (c) into a binary image;
  d. smoothing binarized image as obtained in step (c) by Gaussian Smoothing technique;
  e. recognizing circle bond to identify presence of a circle inside a ring;
  f. predicting Optical Character Recognition (OCR) region to find zones containing text;
  g. thinning the image to identify specific shapes within said binary image;
  h. detecting edge of the image by using sobel operator, canny edge detector or by similar tools;
  i. detecting double and triple bond; and
  j. obtaining output files in .mol, .sdf or similar format.

In yet another embodiment, double bond and triple bond are detected by using distance formula.

In yet another embodiment, .mol file format provides a connection table, which identify the chemical context of the texts and graphics included in the image.

BRIEF DESCRIPTION OF THE FIGURES

FIG. 7 illustrates a .mol file.

FIG. 18: Output data generated by the image recognition program

DETAILED DESCRIPTION OF THE INVENTION

A method of extracting and then reusing/remodeling chemical data from a hand written or digital, input image without manual inputs using Chemical Structure Recognition Tool (CSRT) is disclosed. The data in the image is suitably manipulated to make analyzable. Analysis is carried out to identify molecular structure, chemical formulae and any other significant chemical data. The information identified is then converted to a suitable format for reusability in simulation and modeling for various applications.

Chemical Structure Recognition Tool (CSRT) to extract and reuse/remodel chemical data from a hand written or digital input image without manual inputs is disclosed. The tool comprises of an image scanner and a digital image manipulator and analyzer.

Various papers, thesis and researches are made incorporating chemical data which cannot be extracted for simulation and remodeling purposes without manual inputs. Relying on manual inputs leads to a time consuming process which may not be error free. To overcome the drawbacks of the prior art, the present invention discloses a Chemical Structure Identification Tool.

Accordingly, the present invention discloses a method of extracting and then reusing/remodeling chemical data from a hand written or digital input image without manual inputs using Chemical Structure Recognition Tool (CSRT) comprising, loading said input image, converting said input image into a grayscale image i.e. stretching of loaded input image, converting said grayscale image into a binary image i.e. binarisation, smoothing to reduce noise within said binary image, recognizing circle bond to identify presence of a circle inside a ring, predicting OCR region to find zones containing text, image thinning to identify specific shapes within said binary image, edge detection to detect image contrast, detecting double and triple bond, and obtaining output files In another embodiment, A Chemical Structure Recognition Tool (CSRT) to extract and reuse/remodel chemical data from a hand written or digital input image without manual inputs, comprising an image scanner and an image manipulator and analyzer, wherein chemical data being extracted in steps of loading said input image, converting said input image into a grayscale image i.e. stretching of loaded input image, converting said grayscale image into a binary image i.e. binarisation, smoothing to reduce noise within said binary image, recognizing circle bond to identify presence of a circle inside a ring, predicting OCR region to find zones containing text, image thinning to identify specific shapes within said binary image, edge detection to detect image contrast, detecting double and triple bond, and obtaining output files.

Figure 1:
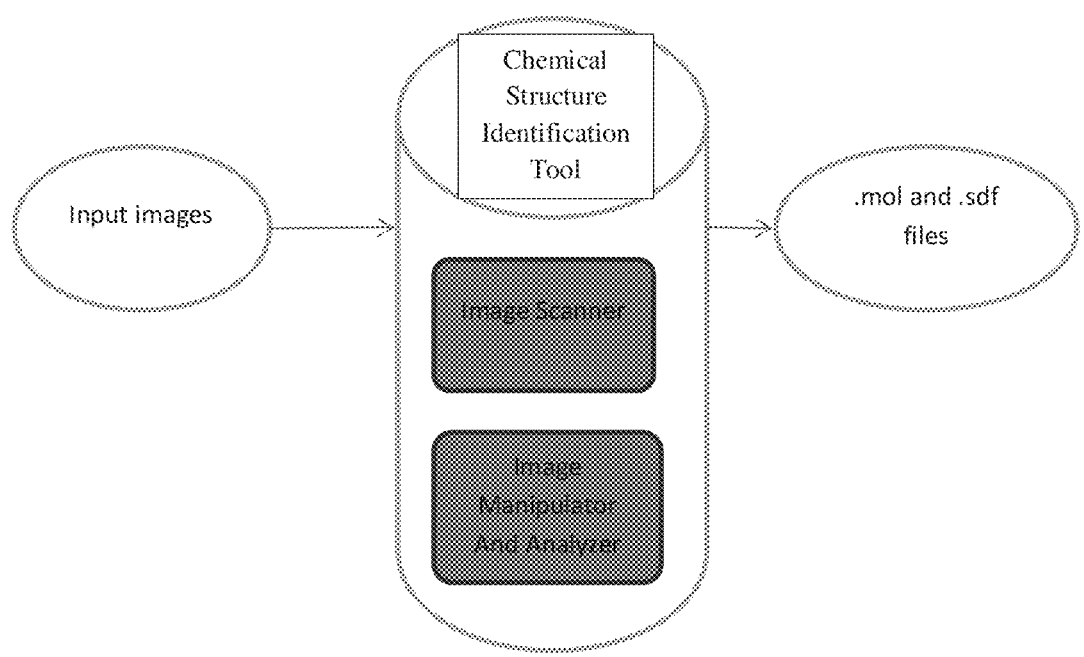
FIG. 1 illustrates a schematic diagram of the present invention.
Figure 2:
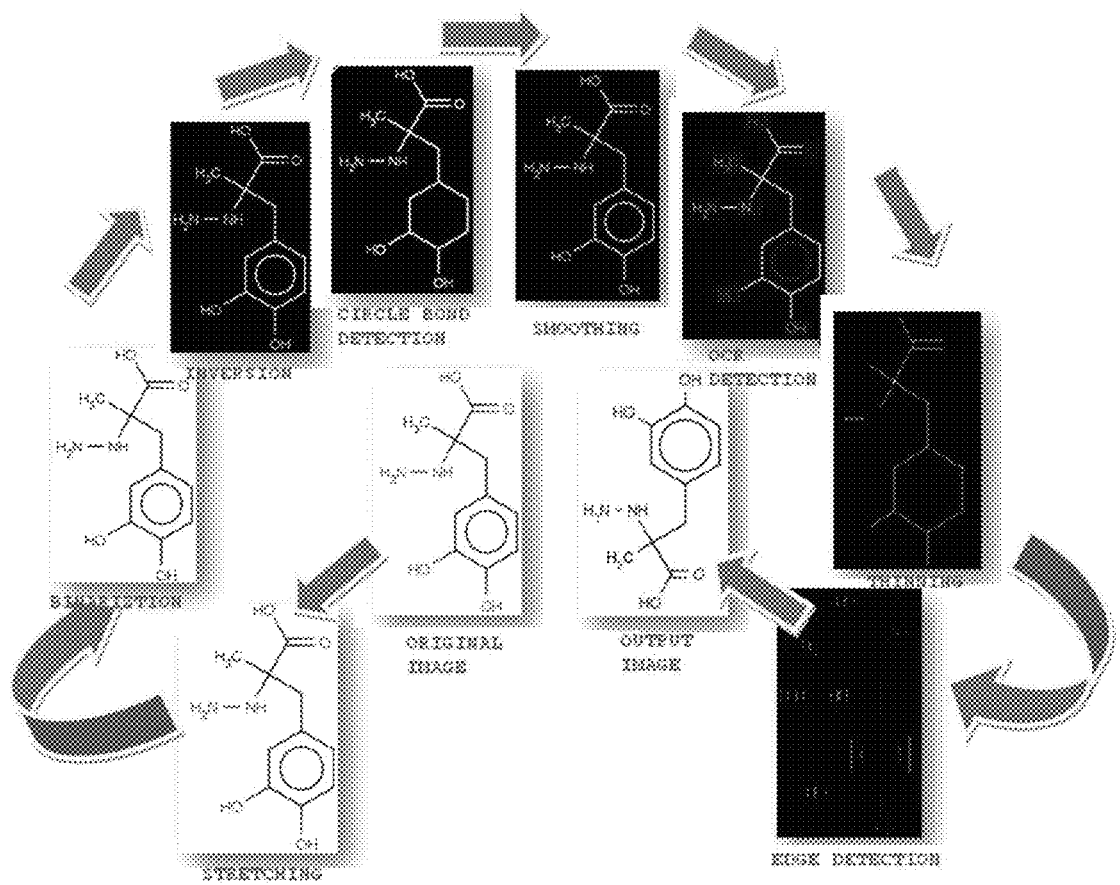
FIG. 2 illustrates a schematic flow of the process of the present invention.

As illustrated in FIG. 1, the Chemical Structure Recognition Tool (CSRT) comprises an image scanner and an image manipulator and analyzer. The image scanner accepts inputs in form of image, such as an image taken from a video frame or photograph, and provides output as a digital image or characteristics associated with such an image.

The recognition of a molecule from a chemical drawing requires the extraction of three kinds of information namely, Atom information, Bond information and Structure information. The CSIT involves the following steps:

1) Capture the image from live camera
2) Noise Reduction algorithm
3) Extraction of chemically significant image from noisy data
4) Identification of edges and nodes
5) Atom symbol recognition
6) Build the connection tables
7) Clustering to connect the nodes based on nearest neighbors
8) Build the atom matrix and connection tables to generate standard file formats (mol, sdf)

Types of Methods Used for Image Processing

1) Analog or Visual Technique: to utilize hard copies like printouts and photographs.
2) Digital Processing Techniques: to facilitate manipulation of the digital images using microprocessors and microcontrollers.

1) Loading an Image

Figure 3:
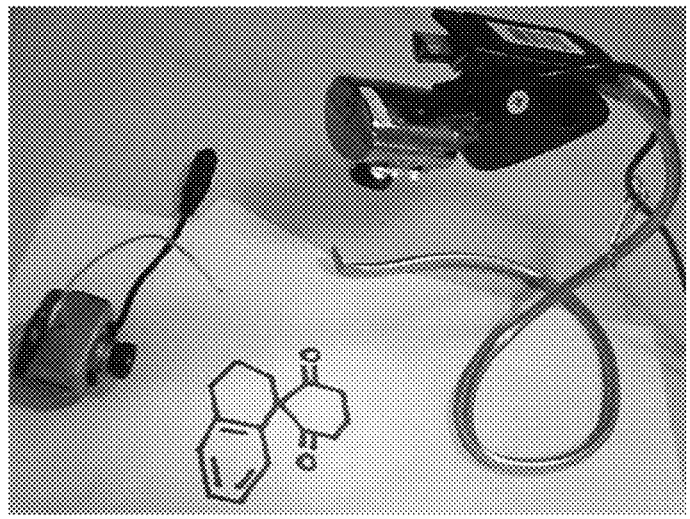
FIG. 3 illustrates experimental setup of the present invention.
Figure 3:
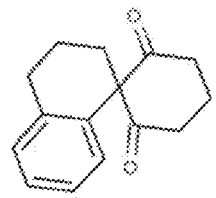
Figure 3:
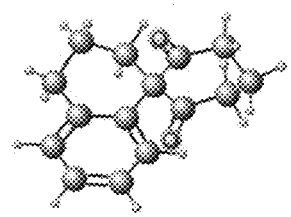

An image is loaded into the CSIT, typically by an input device that may be a Webcam or camera of mobile devices, to produce the image and feed it via a frame grabber board into the memory of the image manipulator and analyzer. It is illustrated in FIG. 3. Other image sources may be stored images that are fed directly into the computer memory.

All the sources input images in JPEG, PNG or GIF format to the CSIT.

2) Stretching of the Image

The loaded image is converted into Grayscale. The averages of the color values are considered as weighted averages to account for human perception to accommodate sensitivity of human perception to green over other colors, green is weighted most heavily.

The conversion coefficients are:
Red: 0.2125;
Green: 0.7154;
Blue: 0.0721.

The standard for luminosity is considered as 0.21 R+0.71 G+0.07 B.

[Note: The image filter accepts 24, 32, 48 and 64 bits per pixel color images and produces a grayscale image of 8 (if source is 24 or 32 bits per pixel image) or 16 (if source is 48 or 64 bits per pixel image) bits per pixel.]

3) Binarization

During Binarization, a grayscale image is converted to a bi-level image (Black & White) by classifying every pixel as an on-pixel (Black) or as an off-pixel (White). The binarization is carried out by regular thresholding, which determines a specified threshold and separates image's pixels into black and white pixels accordingly. Binary system is used to calculate the threshold automatically. The specified threshold is determined as follows:

a) Two gradients are calculated—

$$ex=|I(x+1,y)-I(x-1,y)|x,y+ \text{ and } |I(1)-I(x,y-1)|;$$

x,y are pixel coordinates.
b) Weight is calculated as maximum of two gradients;
c) Sum of weights is updated $$\text{weightTotal}+=\text{weight};$$

d) Sum of weighted pixel values is updated $$\text{total}+=\text{weight}*I(x,y)$$

e) The result threshold is calculated as sum of weighted pixel values divided by sum of weight.

[Note: The filter accepts 8 bpp grayscale images for processing]

Binary image formed during binarization process is inverted and creates a dark background (inverted) image. This image is further smoothened.

4) Smoothing of the Image

Figure 11:
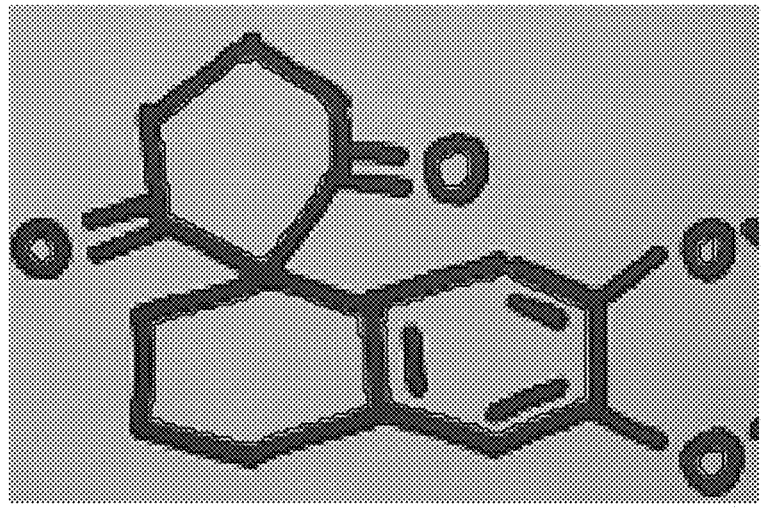
FIG. 11: Identification of outline
Figure 12:
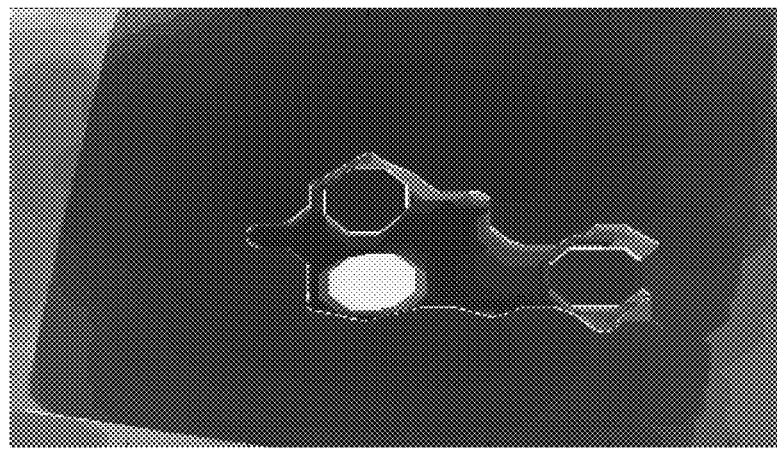
FIG. 12: Identification and Exclusion of background Noise (Computer Vision)
Figure 13:
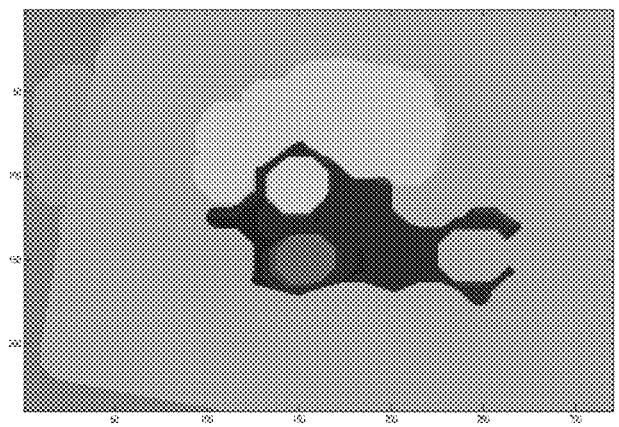
FIG. 13: Normalization of Background noise for exclusion
Figure 14:
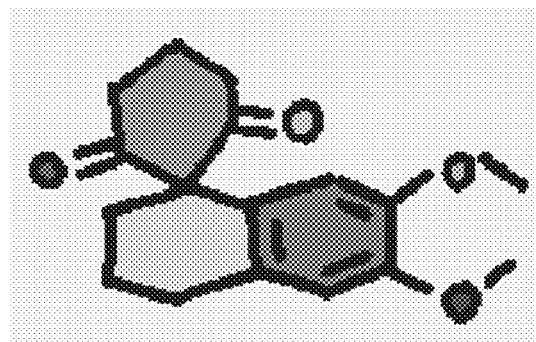
FIG. 14: Chemically significant Regions identified by the algorithm (Excluded background)

Smoothing is performed on the image resultant of step 4 to reduce noise within an image or to produce a less pixilated image. This is illustrated in FIGS. 11 & 12. A low pass filter is utilized to perform smoothening. An image is smoothed by decreasing the disparity between pixel values by averaging nearby pixels. Using a low pass filter, the low frequency information is retained within an image while reducing the high frequency information.

Gaussian Smoothing:

In Gaussian Smoothing technique, Gaussian Function is applied on the image which results in blurring of the image, to reduce image noise and reduce detail.

The equation of Gaussian Function in one dimension:

$$G(x) = \frac{1}{\sqrt{2\pi\sigma 2}} e^{-\frac{x2}{2\pi\sigma 2}},$$

In two dimensions $$G(x, y) = \frac{1}{\sqrt{2\pi\sigma 2}} e^{-\frac{x2+y2}{2\pi\sigma 2}},$$

where x is the distance from the origin in the horizontal axis, y is the distance from the original in the vertical axis, and σ is the standard deviation of the Gaussian distribution.

5) Circle Bond Recognition

If a circle is found inside of a ring, the atoms around the circle forming ring is considered to be an aomatic system. It is assumed that in a circle, all edge points have the same distance to its centre, which equals to circle's radius. Owing to distortions due to different image processing techniques, some edge pixels may be closer or further to circle's centre. This variation in distance to the centre is permissible in a predefined limited range. If the distance varies beyond the range, then it is considered that the object may not be circular.

Further analysis is performed on the estimated circle's radius and centre (X):distance to the estimated centre is calculated and the difference with estimated radius is checked i.e. distance between provided edge points (A, B, C, D, E & F) and estimated circle as in FIG. 3. Instead of checking each individual distance value for each edge pixel, mean distance is calculated.

Figure 4:
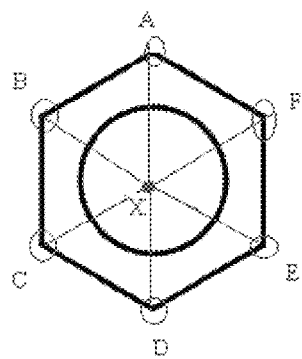
FIG. 4 illustrates calculation of distance of points of circle from the edges.

Further, calculated mean distance between provided shape's edge points and estimated circle, it is checked if the value falls into certain range. If it exceed vastly, then it means that the specified shape is not a circle, since its edge points are quite away on the average from the estimated circle. Ideally the value should be close to 0, meaning that all specified edge points fit very well the estimated circle. The distortion limit for circle shapes is dependant on the shape's size, so as to allow higher level of distortion for bigger shapes and lower value of distortion for smaller shapes. This is illustrated in FIG. 4.

For example, distortion level may be calculated as follows:

In the case of small circles, like 10×10 pixels in size, the calculated distortion limit may be equal to 0.3. If a circle has some little distortion, then it may not be recognized as circle. For example, for circles which are 9×10 or 11×10 in size, calculations may lead to higher distortion than the specified limit. To avoid this, an additional parameter is added which is minimum acceptable distortion.

6) Optical Character Recognition (OCR) Region Prediction

OCR Technology typically segments the page image into zones, primarily with the purpose of finding zones that contain text for character recognition. Blob Function is performed on connected components classified as characters. Individual characters are assembled into character strings based on XY coordinates, that is, the XY positions of various individual characters are compared and character strings are assembled based primarily on adjacency of the coordinates.

General Optical Character Recogntion (GOCR), method is used to find the text or characters present in the OCR region and save them. It is a command line program to facilitate recognition of characters from an image file.

7) Thinning of an Image

The hit-or-miss morphological operation is used primarily for identifying specific shapes within binary images. The operation first applies an erosion operation with the hit structure to the original image. The operation then applies an erosion operator with the miss structure to an inverse of the original image. The matching image elements entirely contain the hit structure and are entirely and solely contained by the miss structure.

The hit-or-miss operation is very sensitive to the shape, size and rotation of the two structuring elements. Hit and miss structuring elements must be specifically designed to extract the desired geometric shapes from each individual image. When dealing with complicated images, extracting specific image regions may require multiple applications of hit and miss structures, using a range of sizes or several rotations of the structuring elements.

8) Edge Detection

Figure 15:
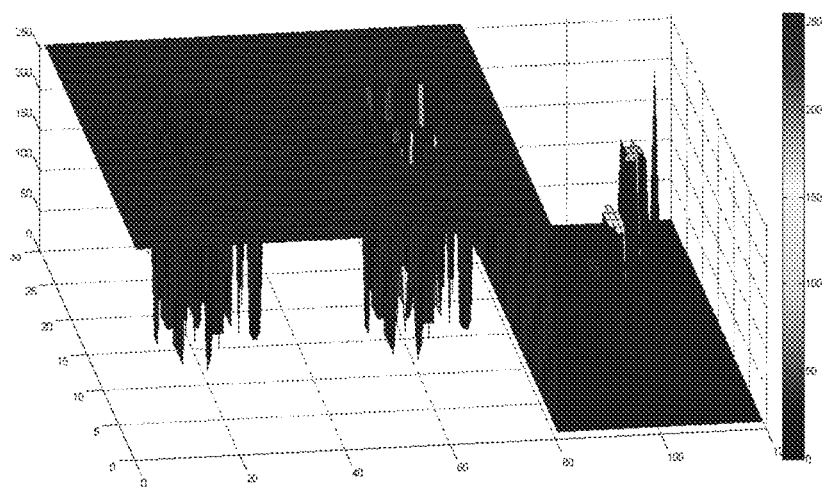
FIG. 15: Computer Vision of Normalized image (excluded background)
Figure 16:
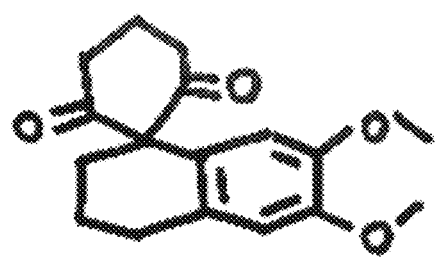
FIG. 16: Final image in black and white for identification of edges and nodes
Figure 17:
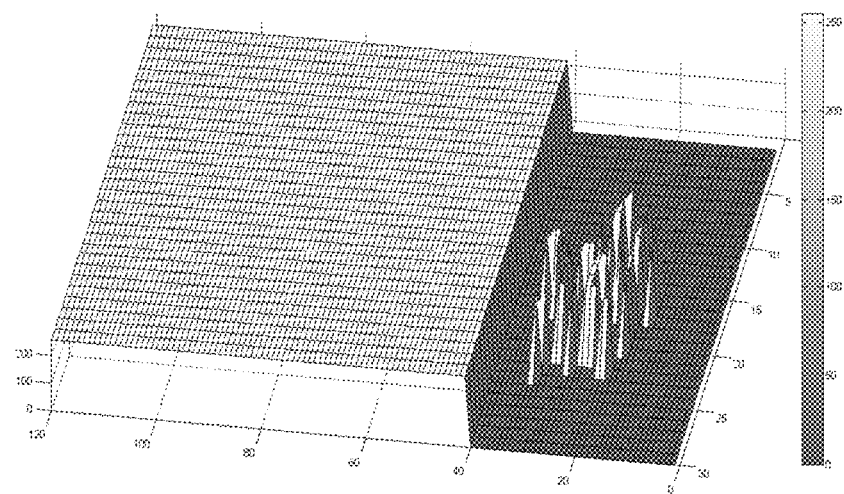
FIG. 17: Computer Vision of black and white image
Figure 19:
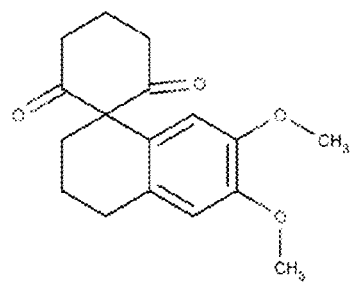
FIG. 19: Visualization of output files in standard chemical information processing tools
Figure 20:
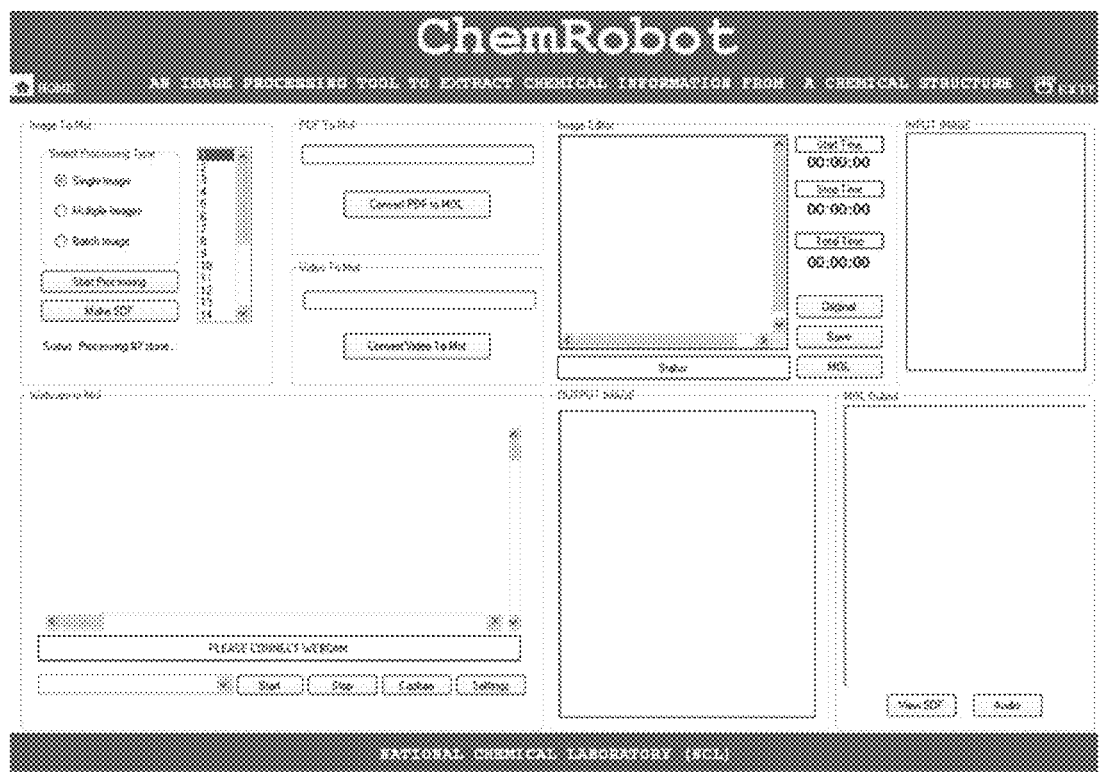
FIG. 20: User Interface

Edge Detection highlights image contrast. Detecting contrast, which is difference in intensity, can emphasize the boundaries of features within an image. the boundary of an object is a step change in the intensity levels. The Edge is at the position of the step change. It is illustrated in FIG. 15.

Edge Detection Techniques

SOBEL OPERATOR: The Sobel operator is utilized to find contrast by a process akin with differentiation. The magnitude of the edges is detected by convolving two 3*3 templates with the grey level image.

The operator consists of a pair of 3×3 convolution kernels, one kernel rotated by 90 degrees to obtain the other. These kernels are designed to respond maximally to edges running vertically and horizontally relative to the pixel grid, one kernel for each of the two perpendicular orientations. The two kernels may be applied separately to the input image to produce separate measurements of the gradient component in each orientation [Mx&My] and these kernels combine together to find the absolute magnitude of the gradient at each point and orientation of that gradient.

| −1 | 0 | +1 |
|---|---|---|
| −2 | 0 | +2 |
| −1 | 0 | +1 |

Mx

| +1 | +2 | +1 |
|---|---|---|
| 0 | 0 | 0 |
| −1 | −2 | −1 |

My

The edge detection operator returns a value for the first derivative in the horizontal direction (My) and the vertical direction (Mx). From this the edge gradient and direction can be determined:

$$|M|=|Mx|+|My|$$

Edge Gradient is given by:

$$|M|=\sqrt{Mx^2+My^2}$$

And, the direction:

$$\theta = \arctan\left(\frac{Gy}{Gx}\right)$$

The edge direction angle is rounded to one of four angles representing vertical, horizontal and the two diagonals.

Canny Edge Detection

The following are requisite considerations:

1. Low Error Rate:

It is important that edges occurring in images should not be missed and there be no responses to non-edges.

2. The edge points are well localized.

The distance between the edge pixels as found by the detector and the actual edge is to be at a minimum.

3. One response to a single edge.

Based on the above requisites, canny edge detector is first used to smoothen the image to eliminate end noise. Image gradient is then found to highlight regions with high special derivative. The gradient array is now further reduced by hysteresis. Hysteresis is used to track along the remaining pixels that have not been suppressed. Hysteresis uses two thresholds and if the magnitude is below the first threshold, it is set to be not zero (made a non-edge). If the magnitude is high threshold, it is made an edge. And if the magnitude is between two thresholds, that it is set to zero unless it is path from this pixel to a pixel with a gradient above threshold two (high and low).

In order to implement the canny edge detector algorithm, a series of steps must be followed.

1) First, to filter out any noise in original image before trying to locate and detect any edges, Gaussianfilter is extensively used, as it can be computed using single mask. Once a suitable mask is calculated, the Gaussian smoothing may be performed using standard convolution methods. The larger the width of Gaussian mask, the lower is the detector's sensitivity to noise. The localization error in the detected edges also increase as the Gaussian width is increased 2) After smoothing image and eliminating the noise, the edge strength is found by taking gradient of the image. The sobel operator is used to perform a 2-D special gradient on an image. Then, the approximate value gradient magnitude (edge strength) at each point is found.

The magnitude or edge strength (M) is given by:

$$|M| = \sqrt{Mx^2 + My^2}$$

3) The direction of the edge is computed using the gradient in the x and y directions. However an error will be generated when sumx is equal to zero. a restriction is set to check such a condition. Whenever the gradient in the x direction is equal to zero, the edge direction has to be equal to 90 degrees or 0 degrees. The formula for finding the edge direction is given by $$\theta = \arctan\left(\frac{Gy}{Gx}\right)$$

4) Once the x direction is known the next step is to relate the edge direction to a direction that can be traced in an image.
5) After the edge directions are known non-maximum suppression is applied. Non maximum suppression is used to trace along the edge in the edge direction and suppress any pixel value that is not considered to be an edge. This gives a thin line in the output image.
6) Finally, hysteresis is used as a means of elimination streaking. Streaking is the breaking up of image contour caused by the operator output fluctuating above and below the threshold. If a single threshold t1 is applied to an image and an edge has an average strength=t1, then due to noise there will be instances where the edge bits below the threshold. Equally it will also extend above the threshold making an edge look like a dashed line. To avoid this, hysteresis uses two thresholds a high and low. Any pixel in the image that has a value greater then t1 is presumed to be an edged pixel, and is marked. Then any pixels that are connected to this edge pixel and have a value greater then t2 are also selected as edge pixels.

9) Double and Triple Bond Detection

The double and triple bonds are identified as bond pairs (triples) which:
   a) are parallel to each other,
   b) are within the double bond pair distance of each other, and
   c) are within each other's "shadow"—that is the bonds of the bond pair are not separated too far along the line parallel to them.

Two parallel lines in a plane are parallel if they are everywhere equidistant.

To measure the distance between two parallel lines, we can measure the distance between one of the lines and any point on the other, as illustrated in FIG. 4.

It is given by Distance Formula:

$$x = \sqrt{(a2-a1)^2 + (b2-b1)^2}$$

$$y = \sqrt{(c2-c1)^2 + (d2-d1)^2}$$

Figure 5:
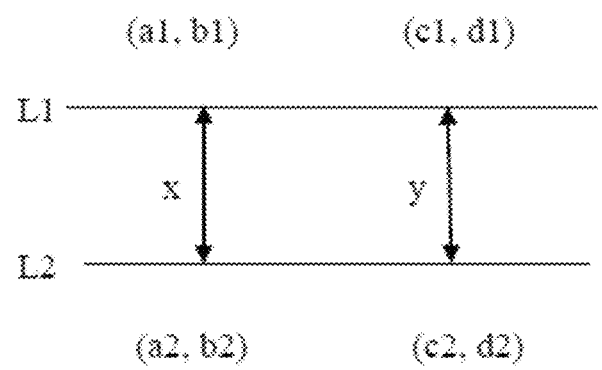
FIG. 5 illustrates verification of parallel lines when they are equal in length.

If two lines (L1, L2), are of equal length
If x=y then, two lines are parallel.
If two lines (L1, L2) are of different size, then as illustrated in FIG. 5, $$z1 = \overline{\phantom{xxxxxxxx}}$$

$$z2 = \overline{\phantom{xxxxxxxx}}$$

On comparing z1 & z2,
If z1=z2 then, L1 &L2 are two parallel lines.
If z1<z2, and z1+5≤z2 then, L1 &L2 are two parallel lines.
If z1>z2, and z2+5≤z1 then, L1 &L2 are two parallel lines.

10) Output Files

Figure 6:
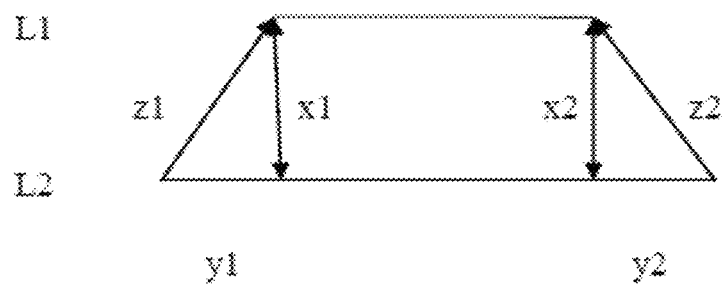
FIG. 6 illustrates verification of parallel lines when they are unequal in length.
Figure 8:
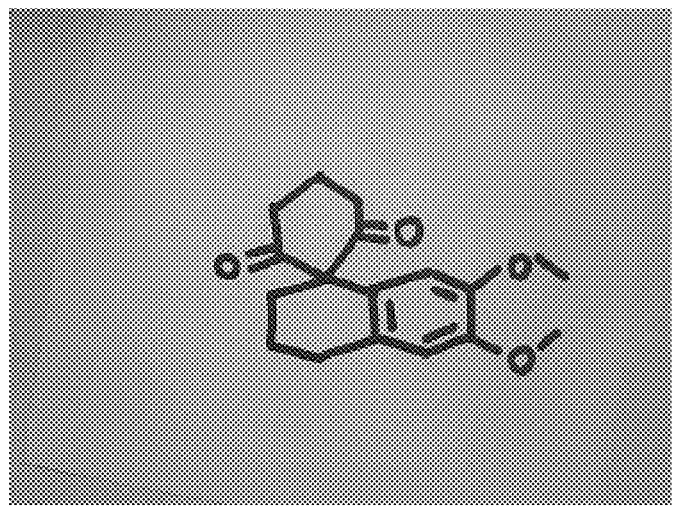
FIG. 8: Original Image captured by the digital device for Human Perception
Figure 9:
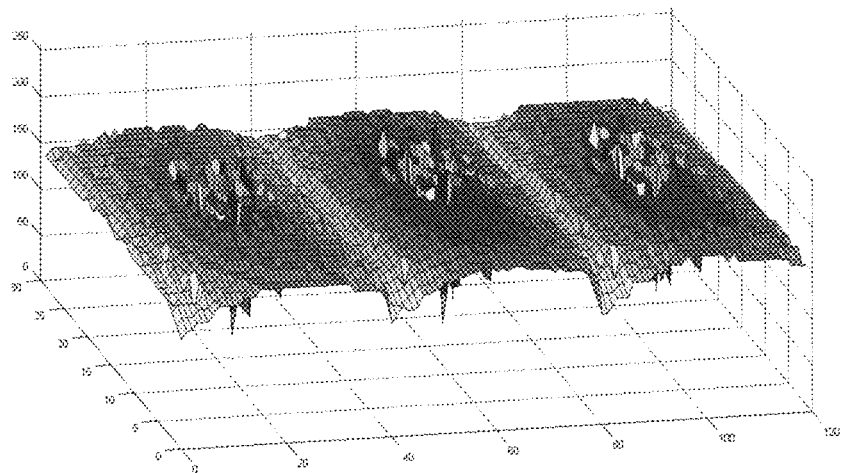
FIG. 9: Machine Vision (Depth, color, Intensity) for Processing
Figure 10:
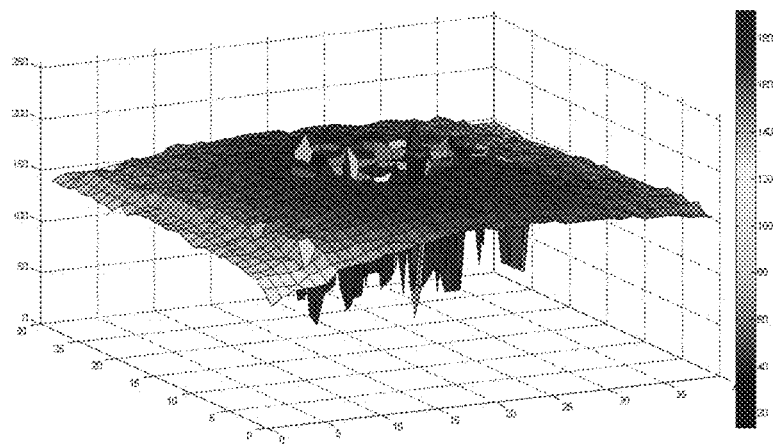
FIG. 10: Computer Vision (Content and Background) for Processing

The output files comes in two formats .mol files and .sdf format as illustrated in FIG. 6 and FIG. 7, respectively. The .mol format provides a connection table, which correctly identify the chemical context of the texts and graphics included in an image.

The process of achieving the final outputs .mol and .sdf files is mentioned using certain methods as described hereinabove. It may be appreciated by a person skilled in the art that, the said process may be suitably modified with relative advancement in its contributing methods.

FIGS. 7 to 19 depict the steps involved in the Chemical Structure Recognition Tool of the invention.

TABLE 1

| Examples | Loaded Image | Obtained image |
|---|---|---|
| | Examples 1 to 11 | |
| Example 1 | *(image)* | *(chemical structure)* |

TABLE 1-continued
Examples 1 to 11
| Examples | Loaded Image | Obtained image |
| --- | --- | --- |
| Example 2 | 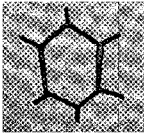 | 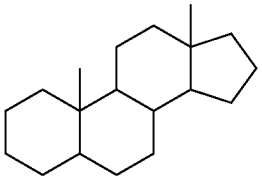 [SMILES: CC12CCCC1C1CCC3CCCCC3(C)C1CC2] |
| Example 3 | 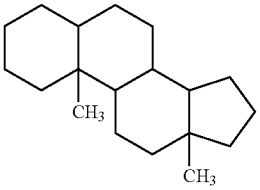 [SMILES: CC12CCCC1C1CCC3CCCCC3(C)C1CC2] | 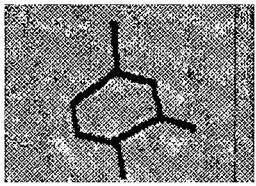 |
| Example 4 | 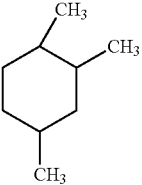 | 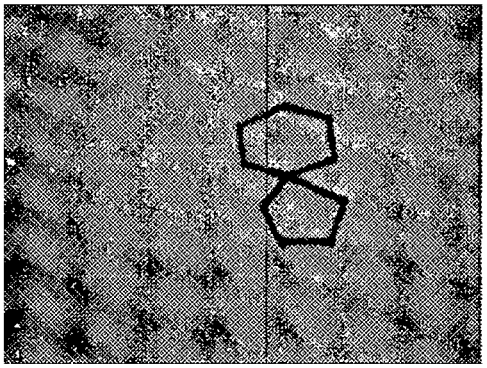 |
| Example 5 |  | 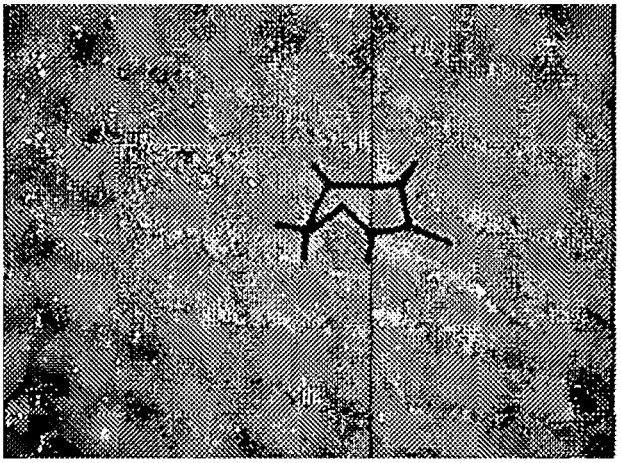 |
| Example 6 | 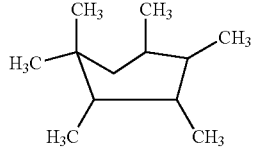 | |

TABLE 1-continued

Examples 1 to 11

| Examples | Loaded Image | Obtained image |
|---|---|---|
| Example 7 | | hexagon |
| Example 8 | | cyclohexane with two CH$_3$ groups (1,3-dimethylcyclohexane) |
| Example 9 | | decahydronaphthalene with eight CH$_3$ substituents |
| Example 10 | | C(CH$_3$)$_3$ (isobutyl-like structure with three CH$_3$ groups) |

TABLE 1-continued

Examples 1 to 11

| Examples | Loaded Image | Obtained image |
|---|---|---|
| Example 11 | (image of noisy background with zigzag structure) | H₃C–(zigzag chain)–CH₃ |

Following are the sample list of totally failed images tested with OSRA which were successfully translated into truly computable format by OSRT (chemrobot).

TABLE 2

FIGS. -1 (Image Id 17_34_09)

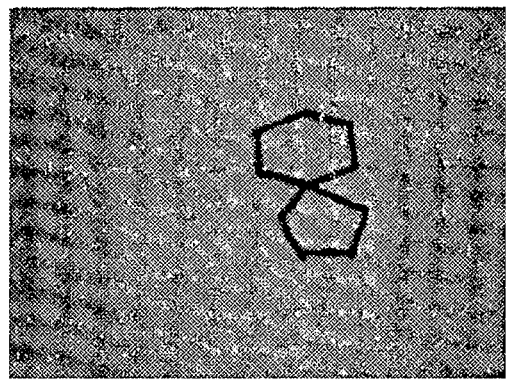

```
chemrobot@NCL-Pune-India 23081117342D
 10 13  0  0  0            999 V2000
   -3.3200   -1.1200    0.0000 C   0  0  0  0  0  0  0  0  0
 0  0
   -3.1100   -0.7300    0.0000 C   0  0  0  0  0  0  0  0  0
 0  0
   -3.6500   -1.6400    0.0000 C   0  0  0  0  0  0  0  0  0
 0  0
   -3.7200   -2.2500    0.0000 C   0  0  0  0  0  0  0  0  0
 0  0
   -3.0600   -2.5400    0.0000 C   0  0  0  0  0  0  0  0  0
 0  0
   -2.4500   -2.3700    0.0000 C   0  0  0  0  0  0  0  0  0
 0  0
   -2.3400   -1.2100    0.0000 C   0  0  0  0  0  0  0  0  0
 0  0
   -3.0100   -1.5000    0.0000 C   0  0  0  0  0  0  0  0  0
 0  0
   -2.3700   -1.8000    0.0000 C   0  0  0  0  0  0  0  0  0
 0  0
   -2.3800   -0.7800    0.0000 C   0  0  0  0  0  0  0  0  0
 0  0
  1  2  1  0  0  0  0
  3  4  1  0  0  0  0
  1  2  1  0  0  0  0
  5  6  1  0  0  0  0
  7  8  1  0  0  0  0
  6  9  1  0  0  0  0
  7 10  1  0  0  0  0
  3  8  1  0  0  0  0
  2 10  1  0  0  0  0
  8  9  1  0  0  0  0
  1  8  1  0  0  0  0
  4  5  1  0  0  0  0
 10  7  1  0  0  0  0
M END
```

TABLE 2-continued
FIGS. -1 (Image Id 15_20_52)
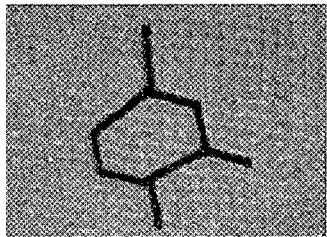
```
chemrobot@NCL-Pune-India 23081117202D
  9  9  0  0  0  0            999 V2000
   -5.5400   -3.1300    0.0000 C   0  0  0  0  0  0  0  0  0  0  0  0
   -5.8600   -3.2100    0.0000 C   0  0  0  0  0  0  0  0  0  0  0  0
   -5.4300   -2.8700    0.0000 C   0  0  0  0  0  0  0  0  0  0  0  0
   -5.1600   -2.7200    0.0000 C   0  0  0  0  0  0  0  0  0  0  0  0
   -5.9100   -2.6200    0.0000 C   0  0  0  0  0  0  0  0  0  0  0  0
   -6.2700   -2.9600    0.0000 C   0  0  0  0  0  0  0  0  0  0  0  0
   -6.2000   -2.6600    0.0000 C   0  0  0  0  0  0  0  0  0  0  0  0
   -5.7500   -2.3100    0.0000 C   0  0  0  0  0  0  0  0  0  0  0  0
   -5.8500   -3.7300    0.0000 C   0  0  0  0  0  0  0  0  0  0  0  0
  1  2  1  0  0  0  0
  1  3  1  0  0  0  0
  4  3  1  0  0  0  0
  5  3  1  0  0  0  0
  6  2  1  0  0  0  0
  5  7  1  0  0  0  0
  7  6  1  0  0  0  0
  5  8  1  0  0  0  0
  9  2  1  0  0  0  0
M  END
```
FIGS. -1 (Image Id 15_20_19)
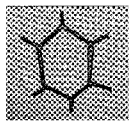
```
chemrobot@ncl-pune 10191017012D
 12 12  0  0  0  0            999 V2000
   -5.6800   -3.9400    0.0000 C   0  0  0  0  0  0  0  0  0  0  0  0
   -5.6600   -3.7600    0.0000 C   0  0  0  0  0  0  0  0  0  0  0  0
   -5.3700   -3.0200    0.0000 C   0  0  0  0  0  0  0  0  0  0  0  0
   -5.3700   -3.5100    0.0000 C   0  0  0  0  0  0  0  0  0  0  0  0
   -5.5400   -2.8100    0.0000 C   0  0  0  0  0  0  0  0  0  0  0  0
   -5.5500   -2.6600    0.0000 C   0  0  0  0  0  0  0  0  0  0  0  0
   -5.9600   -2.9900    0.0000 C   0  0  0  0  0  0  0  0  0  0  0  0
   -6.0200   -3.4800    0.0000 C   0  0  0  0  0  0  0  0  0  0  0  0
   -5.0600   -2.9700    0.0000 C   0  0  0  0  0  0  0  0  0  0  0  0
   -6.0400   -2.8500    0.0000 C   0  0  0  0  0  0  0  0  0  0  0  0
   -5.1200   -3.6600    0.0000 C   0  0  0  0  0  0  0  0  0  0  0  0
   -6.2500   -3.6000    0.0000 C   0  0  0  0  0  0  0  0  0  0  0  0
  1  2  1  0  0  0  0
  3  4  1  0  0  0  0
  5  6  1  0  0  0  0
  7  8  1  0  0  0  0
  3  9  1  0  0  0  0
  3  5  1  0  0  0  0
  7  5  1  0  0  0  0
  7 10  1  0  0  0  0
  4 11  1  0  0  0  0
  2  8  1  0  0  0  0
  8 12  1  0  0  0  0
  2  4  1  0  0  0  0
M  END
```

TABLE 2-continued

FIGS. -1 (Image Id 17_40_42)

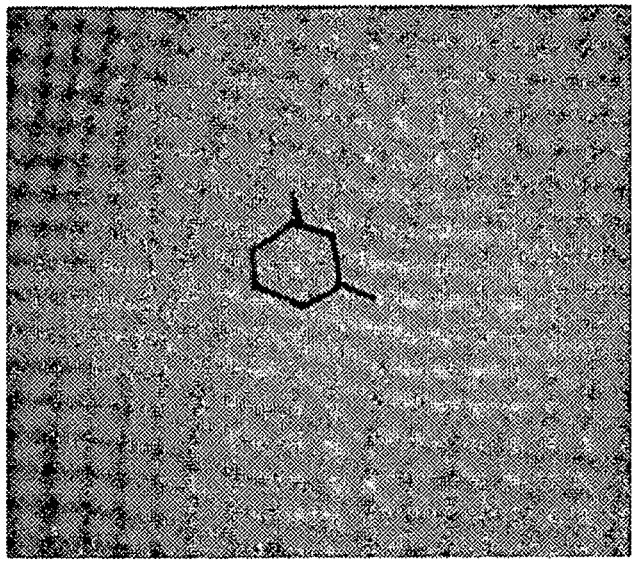

```
chemrobot@ncl-pune 11051101112D
 8  8  0  0  0  0            999 V2000
   -8.6179   -3.0998    0.0000 C  0 0 0 0 0 0 0 0 0 0
 0 0
   -9.4093   -2.6382    0.0000 C  0 0 0 0 0 0 0 0 0 0
 0 0
   -8.9036   -4.0452    0.0000 C  0 0 0 0 0 0 0 0 0 0
 0 0
   -9.5632   -4.2430    0.0000 C  0 0 0 0 0 0 0 0 0 0
 0 0
   -7.9583   -2.9019    0.0000 C  0 0 0 0 0 0 0 0 0 0
 0 0
   -9.5412   -4.9465    0.0000 C  0 0 0 0 0 0 0 0 0 0
 0 0
  -10.3326   -3.0778    0.0000 C  0 0 0 0 0 0 0 0 0 0
 0 0
  -10.4425   -3.8033    0.0000 C  0 0 0 0 0 0 0 0 0 0
 0 0
 1 2 1 0 0 0 0
 3 4 1 0 0 0 0
 1 5 1 0 0 0 0
 6 4 1 0 0 0 0
 3 1 1 0 0 0 0
 2 7 1 0 0 0 0
 8 4 1 0 0 0 0
 7 8 1 0 0 0 0
 M END
```

Recognition rate in automatic mode is improved to 70% from original 30% by optimization.

ADVANTAGES OF THE INVENTION

The advantages of the present invention are as follows:
1) It teaches the method to extract chemical structure from hand-drawn images and not only from computer generated images as discussed in the prior art documents. A hand-drawn chemical structure captured by an optical device such as webcam is particularly difficult because of realistic conditions such as background, human errors etc. Thus the inventive step of the present invention lies in extracting image of hand-drawn chemical structure captured by live camera.
2) It covers various aspects of extracting hand-drawn chemical structures such as colour handling, light intensity, ambience, distance between objects and light sources, quality of optical imaging with respect to output image.
3) It can be useful in drug discovery process.
4) It can find use in e-learning and distance learning applications.

I claim:
1. A Chemical Structure Recognition Tool (CSRT) to extract chemical data from an input image of a hand drawn chemical structure, said Chemical Structure Recognition Tool comprising an image scanner, and an image manipulator and analyzer coupled to the image scanner, wherein:
the image scanner is to receive a live feed of the input image from a camera and load the input image into the image manipulator and analyzer, wherein the input image is one of a photograph and a video frame of the hand drawn chemical structure sketched on a surface and captured live by the camera; and
the image manipulator and analyzer is to:
convert each color pixel of said input image into a grayscale pixel using color conversion coefficients and normalize each pixel for obtaining a grayscale image with chemically significant regions highlighted, wherein the color conversion coefficients include a red color conversion coefficient of 0.2125, a green color conversion coefficient of 0.7154, and a blue color conversion coefficient of 0.0721;
binarize said grayscale image into a binary image;
smoothen said binary image by Gaussian Smoothing;
extract chemical data from the smoothened input image by:
recognizing a shape in said binary image to be a circle to identify presence of a circle bond inside a ring;
predicting an Optical Character Recognition (OCR) region to find zones containing text;
thinning the binary image using a hit or miss morphological operation to identify specific shapes within said binary image;
detecting edges of the image by using at least one of sobel operator and canny edge detector; and
detecting a double bond and a triple bond; and
obtain output files in a digital format with the extracted chemical data from the input image.
2. The Chemical Structure Recognition Tool as claimed in claim 1, wherein the image scanner is an image acquisition tool integrated to at least one of a digital camera, a mobile phone, a phone camera, a computer, and a scanner and wherein the image manipulator and analyzer is a software independent of type of the image scanner.
3. The Chemical Structure Recognition Tool as claimed in claim 1, wherein said input image is accepted and output as a digital image by said image scanner.
4. A method of extracting chemical data from an input image of a hand drawn chemical structure using the Chemical Structure Recognition Tool as claimed in claim 1, the method comprising:
receiving, by an image scanner, a live feed of the input image from a camera, wherein the input image is one of a photograph and a video frame of the hand drawn chemical structure sketched on a surface and captured live by the camera;

loading the input image by the image scanner into an image manipulator and analyzer;

converting each color pixel of said input image into a grayscale pixel using color conversion coefficients and normalizing each pixel to obtain a grayscale image with chemically significant regions highlighted, wherein the color conversion coefficients include a red color conversion coefficient of 0.2125, a green color conversion coefficient of 0.7154, and a blue color conversion coefficient of 0.0721;

binarizing said grayscale image into a binary image;

smoothing said binary image by Gaussian Smoothing;

extracting chemical data from the smoothened input image, the extracting the chemical data comprises:

recognizing a shape in said binary image to be a circle to identify presence of a circle bond inside a ring;

predicting an Optical Character Recognition (OCR) region to find zones containing text;

thinning the binary image using a hit or miss morphological operation to identify specific shapes within said binary image;

detecting edge of the image by using at least one of sobel operator and canny edge detector; and detecting a double bond and a triple bond; and obtaining output files in a digital format with the extracted chemical data from the input image.

5. The method as claimed in claim 4, wherein the double bond and the triple bond are detected by using a distance formula.

6. The method as claimed in claim 4, wherein the output files include a connection table, which identifies chemical context of texts and graphics included in the input image.

7. The method as claimed in claim 4, wherein the shape in the binary image is recognized as the circle by determining that a calculated mean distance between the shape's edge points and an estimated circle lies in a range depending on size of the shape.

8. The method as claimed in claim 4, wherein the digital format is one of .sdf and .mol.

* * * * *